(12) United States Patent
Beck et al.

(10) Patent No.: US 9,512,461 B1
(45) Date of Patent: Dec. 6, 2016

(54) DETECTION OF AFLATOXINS AND AFLATOXIC ASPERGILLI IN NATURAL FUNGAL BOUQUETS

(75) Inventors: John J. Beck, Rocklin, CA (US); Noreen E. Mahoney, Richmond, CA (US)

(73) Assignee: The United States of America, as Represented by the Secretary of Agriculture

( * ) Notice: Subject to any disclaimer, the term of this patent is extended or adjusted under 35 U.S.C. 154(b) by 1357 days.

(21) Appl. No.: 12/895,748

(22) Filed: Sep. 30, 2010

(51) Int. Cl.
*C12Q 1/04* (2006.01)

(52) U.S. Cl.
CPC ........................ *C12Q 1/04* (2013.01)

(58) Field of Classification Search
None
See application file for complete search history.

(56) References Cited

U.S. PATENT DOCUMENTS 4,314,027 A * 2/1982 Stahr .............................. 435/34
4,535,248 A 8/1985 Schade et al.

OTHER PUBLICATIONS

Zeringue et al. J Agric Food Chem., 1996, 44, 403-407.*
Vazquez-Araujo et al. European Food Rsearch and Technology, 2008, 227(1), 243-254.*
Buttery et al. Journal of Agricultural and Food Chemistry, 1980, 28(2), 353-356.*
Zeringue H.J. Canadian Journal of Botany, 1996, 74(1), 98-102.*
Beck, J.J. et al., "Comparison of volatile emissions from undamaged and mechanically damaged almonds" (2008) Journal of the Science of Food and Agriculture, 88:1363-1368.
Campbell, B. C., R. J. Molyneux and T. F. Schatzki, "Current Research on Reducing Pre- and Post-harvest Aflatoxin Contamination of U.S. Almond, Pistachio, and Walnut" (2003) Journal of Toxicology | Toxin Reviews, 22(2&3): 225-266.
Haddon, W. F., M. Wiley and A. C. Waiss, Jr., "Aflatoxin Detection by Thin-Layer Chromatography-Mass Spectrometry" (1971) Analytical Chemistry 43(2):268-270.
Jelen, H. H. and J. Grabarkiewicz-Szczesna, "Volatile Compounds of Aspergillus Strains with Different Abilities to Produce Ochratoxin A" (2005) Journal of Agricultural and Food Chemistry 53(5):1678-1683.
Light, D. M. and J. J. Beck, "Characterization of Microencapsulated Pear Ester, (2E,4Z)-Ethyl-2, 4-decadienoate, a Kairomonal Spray Adjuvant against Neonate Codling Moth Larvae" (2010) Journal of Agricultural and Food Chemistry 58(13):7838-7845.
Mahoney, N. and R. J. Molyneux, "Rapid Analytical Method for the Determination of Aflatoxins in Plant-Derived Dietary Supplement and Cosmetic Oils" (2010) Journal of Agricultural and Food Chemistry 58(7):4065-4070.
Molyneux, R.J. et al., "Mycotoxins in edible tree nuts" (2007) International Journal of Food Microbiology 119:72-78.
Schnurer, J., J. Olsson and T. Borjesson, "Fungal Volatiles as Indicators of Food and Feeds Spoilage" (1999) Fungal Genetics and Biology 27:209-217.
Scotter, J.M. et al., "Real-time detection of common microbial volatile organic compounds from medically important fungi by Selected Ion Flow Tube-Mass Spectrometry (SIFT-MS)" (2005) Journal of Microbiological Methods 63:127-134.
Sunesson, A. et al., "Identification of volatile metabolites from five fungal species cultivated on two media" (1995) Applied and Environmental Microbiology 61(8):2911-2918.
Wright, M.S., "Effects of volatile aldehydes from Aspergillus-resistant varieties of corn on Aspergillus parasiticus growth and aflatoxin biosynthesis" (2000) Toxicon 38:1215-1223.
Zeringue, H. J. Jr., D. Bhatnagar and T. E. Cleveland, "C15H24 Volatile Compounds Unique to Aflatoxigenic Strain of Aspergillus flavus" (1993) Applied and Environmental Microbiology 59(7):2264-2270.

* cited by examiner

*Primary Examiner* — Vera Afremova
(74) *Attorney, Agent, or Firm* — John D. Fado; Evelyn M. Rabin

(57) ABSTRACT

The present invention relates to food safety and to the reliable detection of aflatoxins produced by aflatoxigenic aspergilli in the presence other fungal species in a natural fungal bouquet using volatile emissions as an indicator.

17 Claims, 4 Drawing Sheets

AFB1

AFB2

AFG1

AFG2

DETECTION OF AFLATOXINS AND AFLATOXIC ASPERGILLI IN NATURAL FUNGAL BOUQUETS

FIELD OF THE INVENTION

The invention relates to the reliable detection of aflatoxigenic Aspergilli in the presence other fungal species in a natural fungal bouquet using volatile emissions as an indicator.

BACKGROUND OF THE INVENTION

Food safety related to contamination of agricultural products by pathogenic fungi is an important concern for the agricultural community. Indeed, pathogenic microbes can contaminate agricultural crops and products and produce acutely poisonous, teratogenic or carcinogenic toxins. Because these toxins pose a grave threat to human, and animal, health, the detection and control of pathogenic fungi and the toxins they produce is imperative.

Particularly egregious pathogenic fungi are the aflatoxigenic aspergilli, *Aspergillus flavus* and *Aspergillus parasiticus*. These fungi are ubiquitous on crop plants important to agriculture, and under favorable conditions of temperature and humidity, are known to produce aflatoxins, which are among the most toxic and carcinogenic substances known to humankind. Among the many ill effects of aflatoxins are acute necrosis, cirrhosis, and carcinoma of the liver. Furthermore, the consumption of large amounts of aflatoxins over a short period of time can result in acute and deadly aflatoxosis. Thus, aflatoxin contamination is a significant food safety issue.

Because aflatoxins are extremely toxic and carcinogenic, strict threshold levels have been set for aflatoxin levels in human consumed food e.g., tree nuts, e.g., almonds, filberts, etc. Thus, in the U. S., the Food Drug Administration (FDA) has set threshold levels for aflatoxins in human consumed food. For example, the FDA has set a level of at 20 parts per billion (ppb) total aflatoxin content for ready to eat almonds, and even more stringent limits have been set in other countries e.g., countries of the European Union.

Aflatoxins are typically detected directly using, for example, thin layer chromatography (TLC), TLC in conjunction with mass spectrometry (see e.g., W. F. Haddon, et al. (1971) *Anal. Chem.,* 43 (2):268-270), HPLC, radioimmunoassay, and enzyme linked immunosorbent assay. The presence of aflatoxins may also be inferred from the from volatile emissions indicative of aflatoxigenic fungi (see e.g., Jelen, H. H.; and Grabarkiewicz-Szczesna, J. (2005) *J. Agric. Food Chem.* 53:1678-1683; Wright, M. S. et al. (2000) *Toxicon* 38:1215-1223; Schnurer, J. et al., (1999) *Fungal Gen. Biol.* 27:209-217; Zeringue, H. J.; et al. (1993) *Appl. Environ. Microbiol.* 59:2264-2270).

Unfortunately, currently used methods are time consuming and rely on the isolation of the aflatoxin or the isolation and cultivation of the aflatoxigenc organism prior to implementation of the analysis (see e.g., Sunesson, A.-L.; et al. (1995) *Appl. Environ. Microbiol.* 61:2911-2918; Scotter, J. M.; et al., (2005) *J. Microbiol. Methods* 63:127-134). Thus, current methods cannot detect aflatoxin contamination early e.g., post harvest when contamination levels are low, and contamination has not spread throughout the entire harvested batch.

Because of the extreme toxicity of aflatoxins, the ubiquity of aflatoxigenic aspergilli on important agricultural crops, the consequences to both human and animal health from aflatoxin ingestion, and the possibility of spread of aflatoxigenic fungi and their associated aflatoxins from a "hot spot" of contamination to an entire batch of agricultural crop, early detection and field detection are imperative. Thus, what is needed in the art, are methods capable of early detection, which can be deployed for rapid, reliable detection under field conditions where the aflatoxin and aflatoxigenic fungi are co-existent with other fungal species in their natural fungal bouquet.

Fortunately, as will be clear from the following disclosure, the present invention provides for these and other needs.

SUMMARY OF THE INVENTION

In one embodiment, the present invention provides A method for detecting the presence of at least one aflatoxin in a crop or crop product, wherein the aflatoxin is produced by an aflatoxigenic *Aspergillus* species, and wherein the aflatoxigenic *Aspergillus* species is co-existent with other fungal species in a natural fungal bouquet. The method comprises: determining a volatile emission profile of the crop or crop product, and comparing the volatile emission profile of the crop or crop product to a volatile emission profile of a control crop or crop product that is known or designated as aflatoxin free, and detecting the presence of at least one unique volatile indicator species in the volatile emission profile of the crop or crop product that is not present in the volatile emission profile of the control crop, wherein the presence of the at least one unique volatile indicator species in the volatile emission profile of the crop or crop product that is not present in the volatile emission profile of the control crop or crop product, indicates that the crop or crop product is contaminated with aflatoxins, wherein the at least one unique volatile indicator species is a member selected from the group consisting of (E)-2-octenal, (E)-2-nonenal, and (E)-2-decenal.

In one exemplary embodiment, the volatile emission profile of the crop or crop product and the volatile emission profile of the control crop or crop product comprise hexanal, heptanal, octanal, 3-octen-2-one, nonanal, and decanal, and wherein the comparing of the volatile emission profile of the crop or crop product to the volatile emission profile of the control crop or crop product reveals that the amount of hexanal, heptanal, octanal, 3-octen-2-one, nonanal, and decanal is increased in the crop or crop product by comparison to the control crop or crop product, thereby indicating that the crop or crop product is contaminated with aflatoxins. In one exemplary embodiment, the amount of hexanal, heptanal, octanal, 3-octen-2-one, nonanal, and decanal is increased in the crop or crop product by at least about 200% by comparison to the control crop or crop product.

In one exemplary embodiment, the crop or crop product is a tree nut crop, and the control crop or crop product that is known or designated to be aflatoxin free is a tree nut crop. In another exemplary embodiment, the tree nut crop is an almond crop, and the control tree nut crop that is known or designated to be aflatoxin free is an almond crop.

In one exemplary embodiment, the volatile emission profile is generated using a Gas Chromatograpy/Mass Spectrometry (GC-MS) instrument. In another exemplary embodiment, the GC-MS instrument is portable.

In one exemplary embodiment, the method is practiced on post harvest tree nuts. In another exemplary embodiment, the post harvest tree nuts are post harvest almonds. In one exemplary embodiment, the post harvest tree nuts are in wind-swept rows. In another exemplary embodiment, the post harvest tree nuts are contained within a storage and/or shipping container.

In one exemplary embodiment, the crop or crop product is cotton and the control crop or crop product is cotton.

In another embodiment the present invention provides a method for detecting the presence of at least one aflatoxin in an almond crop, wherein the aflatoxin is produced by an aflatoxigenic *Aspergillus* species, and wherein the aflatoxigenic *Aspergillus* species is co-existent with other fungal species in a natural fungal bouquet. The method comprises: determining a volatile emission profile of the almond crop, and comparing the volatile emission profile of the almond crop to a volatile emission profile of a control almond crop that is known or designated as aflatoxin free, and detecting the presence of at least one unique volatile indicator species in the volatile emission profile of the almond crop that is not present in the volatile emission profile of the control almond crop, wherein the presence of the at least one unique volatile indicator species in the volatile emission profile of the almond crop that is not present in the volatile emission profile of the control almond crop, indicates that the almond crop is contaminated with aflatoxins, wherein the at least one unique volatile indicator species is a member selected from the group consisting of (E)-2-octenal, (E)-2-nonenal, and (E)-2-decenal.

In one exemplary embodiment, the volatile emission profile of the almond crop and the volatile emission profile of the control almond crop comprise hexanal, heptanal, octanal, 3-octen-2-one, nonanal, and decanal, and wherein the comparing of the volatile emission profile of the almond crop to the volatile emission profile of the control almond crop reveals that the amount of hexanal, heptanal, octanal, 3-octen-2-one, nonanal, and decanal is increased in the almond crop by comparison to the control almond crop, thereby indicating that the almond crop is contaminated with aflatoxins. In one exemplary embodiment, the amount of hexanal, heptanal, octanal, 3-octen-2-one, nonanal, and decanal is increased in the almond crop by at least about 200% by comparison to the control almond crop. In one exemplary embodiment, the volatile emission profile is generated using a Gas Chromatograpy/Mass Spectrometry (GC-MS) instrument. In another exemplary embodiment, the GC-MS instrument is portable.

Other features, objects and advantages of the invention will be apparent from the detailed description which follows.

DETAILED DESCRIPTION OF THE INVENTION

Definitions

Unless defined otherwise, all technical and scientific terms used herein generally have the same meaning as commonly understood by one of ordinary skill in the art to which this invention belongs.

The expression "aflatoxigenic aspergilli" as used herein refers to *Aspergillus* species e.g., *A. flavus* and *A. parasiticus*, that produce, or which are capable of producing, aflatoxins.

Figure 1:
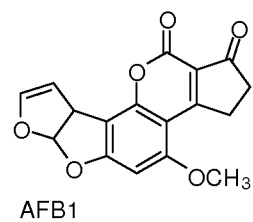
FIG. 1 Structural representation of aflatoxins $B_1$, $B_2$, $G_1$, and $G_2$ (AFB1, AFB2, AFG1, and AFG2, respectively). Aflatoxin $B_1$ and $G_1$ exhibit higher toxicity presumably due to the double bond in the furan ring FIG. 2 Graphic representation of disparities between volatile relative abundances in samples containing no AFG1 and AFG2 compared to samples with some AFG1 and AFG2. Compounds 1, 3, 5, 11, 12, 14, 15, 18, 20, 21, 23, 26, 30, and 32 increased by more than 250% and compounds 16, 24, and 28 corresponding to (E)-2-octenal, (E)-2-nonenal and (E)-2-decenal respectively, were unique to the samples with AFG1 and AFG2. Insert shows expanded area of discreet volatile emissions and unique volatiles.
Figure 1:
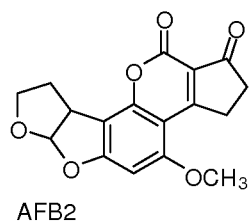
Figure 1:
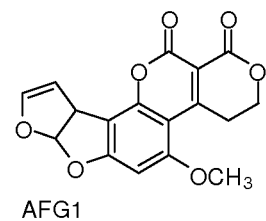
Figure 1:
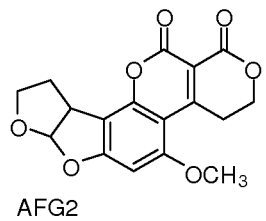

The term "aflatoxin" as used herein, refers to mycotoxins that are members of the difuranocoumarin class of compounds, that can be chemically synthesized, but which are typically produced by a number of species and strains of the genus *Aspergillus*, e.g., *Aspergillus flavus* and *Aspergillus parasiticus*. Exemplary aflatoxins are shown in FIG. 1.

The term "tree nuts" is used herein in its broadest sense to include any hard walled, edible kernel produced by trees. Exemplary "tree nuts" include, but are not limited to e.g., pistachio nuts, almonds, Brazil nuts, pine nuts, chestnuts, walnuts, pecans, peanuts, etc.

The terms "isolated," "purified" or "biologically pure" as used herein, refer to a chemical or microorganism that is substantially or essentially free from components that normally accompany it as found in its native state.

The expression "contaminated tree nut crop" as used herein refers to a tree nut crop, e.g., almonds, that has acquired fungi typically found in tree nut orchards e.g., aspergilli, and/or which has acquired mycotoxins produced by certain of these fungi e.g., mycotoxins produced by aflatoxigenic aspergilli e.g., aflatoxins. Contamination of tree nuts may occur by any means, but typically contamination occurs by way of natural sources e.g., insect damage, transfer in the wind, dust generated by normal orchard service equipment. Contaminated tree nut crops may or may not be contaminated with aflatoxigenic aspergilli. However, in an exemplary embodiment, a contaminated tree nut is contaminated with aflatoxigenic aspergilli e.g., *Aspergillus flavus, Aspergillus paraciticus*. In some exemplary embodiments, a contaminated tree nut crop contaminated with aflatoxigenic aspergilli is also contaminated with aflatoxins.

The expression "natural fungal bouquet" as used herein refers to the set of fungi typically as found in its natural environment (e.g., fungi found in the soil of an orchard) on its natural host and/or food source (e.g., an almond kernel).

Exemplary fungi that may be co-existent with aflatoxigenic aspergilli in a natural fungal bouquet include, but are not limited to *Cladosporium, Penicillium, Apsergillus, Fusarium*, and *Trichoderma*. Thus, an aflatoxic *aspergillus* species in its "natural fungal bouquet" is not "isolated".

An "isolated" microorganism or population of microorganisms means an object microorganism (e.g., an *Aspergillus*) is the predominant microorganism present (i.e., is more abundant than other species in the composition). In an exemplary embodiment, an isolated microorganism comprises at least about 75%, at least about 80%, at least about 85%, at least about 90%, at least about 95% or at least about 99% percent of all microorganisms present.

In some exemplary embodiments, the term "isolated" is used to describe an isolated chemical compound, e.g., isolated aflatoxin. Thus, in some exemplary embodiments, the terms "isolated" or "purified" refer to a chemical species that that is the predominant species present in a preparation. Thus, in some exemplary embodiments, "purity" of an isolated species is determined using analytical chemistry techniques such as e.g., high performance liquid chromatography. A chemical species that is the predominant species present in a preparation is substantially purified. Typically, a "purified" chemical species denotes that a chemical species that is at least about 85% pure, at least about 95% pure, or at least about 99% pure.

The expression "volatile indicator", "indicator volatile", "volatile indicator species" and any grammatically equivalent expression as used herein, refers to a volatile organic compound or compounds that are indicative of the presence of aflatoxins. An "indicator volatile" may be seen only when aflatoxins are present, in which case the "indicator volatile" is a "unique indicator volatile", "unique volatile indicator", "unique volatile indicator species" etc, or the "indicator volatile" may be present in a higher amount or concentration when aflatoxins are present as compared to when aflatoxins are absent.

The expression "volatile emission profile" as used herein refers to the composition of volatile organic compounds emitted by a specific source that are characteristically associated with that specific source under defined conditions. In an exemplary embodiment, a volatile emission profile is reflected in a spectra produced by a GC-MS instrument. An exemplary volatile emission profile is an emission profile of harvested, raw almonds, assumed to be free of microbial contamination, and at room and/or ambient temperature.

I. Introduction:

The potential for microbial and/or fungal toxin (mycotoxin) contamination of crops and crop products is a serious food safety concern. Although most agricultural commodities are known to have ambient microbes associated with them, of particular interest regarding food safety are the aflatoxigenic aspergilli. As discussed above, aflatoxigenic aspergilli are fungi of the genus *Aspergillus* that produce, or are capable of producing aflatoxins.

Aflatoxins are important mycotoxins the ingestion of which can have serious amifications for human health. Long-term exposure to small amounts of aflatoxin, can result in carcinogenesis, and consumption of large amounts of aflatoxin within a short range of time can result in acute aflatoxigenicosis (see e.g., Krishnamachari et al., 1975). Although death caused by aflatoxigenicosis is important in developing countries, the main concern in developed countries with regard to aflatoxin is its insidious property as a potent carcinogen.

There are more than 10 different types of aflatoxins whose structures have a similar difuranocoumarin core. A number of fungal species and strains of the genus *Aspergillus*, e.g., *A. flavus* and *A. parasiticus*, produce aflatoxins as a consequence of normal biosynthetic processes during their growth (see e.g., Smith, J. E. (1994) *Aspergillus*. Plenum Press, NY.; Bennett, J. W. and Klich, M. (2003) *Clin. Microbiol.,* 16: 497-516; Bennett et al., (2007) Aflatoxins: Background, Toxicology, and Molecular Biology. pp. 355-374. In: Shabbir S (ed) Foodborne Diseases. Humana Press, Inc. Totowa, N.J., USA). *A. flavus* is primarily responsible for the production of aflatoxins B1 and B2, and *A. parasiticus* can produce all four aflatoxins AFB1, AFB2, AFG1 and AFG2. Aflatoxins AFB1 and AFG1 are considered to be the most toxic of the four (see e.g., Eaton and Gallagher (1994) *Ann. Rev. Pharmacol. Toxicol.* 34: 135-172).

Aflatoxigenic aspergilli inflict major economic damage to the tree nut industry of California, with a very high negative impact. Aflatoxin contamination of tree nuts in California is not a trivial problem. Indeed, according to the USDA Economic Research Service, California is the Nation's No. 1 producer of tree nuts. Almost 90 percent of U.S. tree nut production is harvested from California orchards annually, including virtually all almonds, pistachios, and walnuts.

Almonds are particularly affected by aflatoxigenic aspergilli. Indeed, approximately 600 samples, translating to 12,000 kg of almonds, are rejected annually due to high levels of aflatoxin contamination. Since California produces 100% of the U.S. supply of commercial almonds, and this, according to the Food and Agriculture Organization (FAO), is 45 percent of the world's production, detecting and controlling aflatoxin contamination on California tree nut crops, especially almond crops, is worldwide concern.

Infection of tree nuts with aflatoxigenic aspergilli probably occurs most often in the field before and/or during harvest while the kernels are still moist (see e.g., U.S. Pat. No. 4,535,248). If infection can be detected early on, and "hot spots" of contamination can be pinpointed, and the infected material removed, large portions of tree nuts can be saved from destruction. Therefore, early aflatoxin detection, especially detection in the field would be avaluable tool indeed.

Although it is known that isolated aspergilli are associated with characteristic volatile profiles when the aspergilli are isolated and cultured under defined conditions, it has not heretofore been appreciated that aflatoxins and aflatoxigenic aspergilli can be reliably detected in the context of their natural environment (i.e., in the presence other fungal species in a natural fungal bouquet) using volatile emissions as an indicator. Thus, until now it has not been possible to detect contamination with aflatoxigenic aspergilli and/or aflatoxins in the field and/or soon after harvest.

Fortunately, as will be disclosed in detail below, it has now been discovered that certain volatiles are indicative of aflatoxins and/or aspergilli when the aflatoxigenic aspergilli are co-existent with other fungi in their natural fungal bouquet. Detection of these volatiles therefore provides for methods that are useful for early aflatoxin detection even under field conditions.

II. Fungi Capable of Producing Mycotoxins on Tree Nut Crops and Crop Products

A. General Methods

Methods disclosed herein utilize routine techniques in the field of chemistry and chemical analysis. Basic texts disclosing the general methods of use in this invention include, e.g., *GC-MSA Practical User's Guide* by Marvin McMaster, Wiley-VCH (1998); *Modern Analytical Chemistry*, by David T. Harvey, McGraw-Hill Science/Engineering/Math (1999).

Methods disclosed herein utilize routine techniques in the field of microbiology. Basic texts disclosing the general methods of use in this invention include, e.g., *Accessing Uncultivated Microorganisms from the Environment to Organisms and Genomes and Back*, Karsten Zengler, ed. ASM Press (2008); *Methods for General and Molecular Microbiology*, 3rd Edition, C. A. Reddy, et al., eds. ASM Press (2008); and *Encyclopedia of Microbiology*, 2nd ed., Joshua Lederburg, ed., Academic Press (2000).

Methods disclosed herein also utilize routine techniques in the field of molecular biology. Basic texts disclosing the general methods of use in molecular biology include e.g., Sambrook et al., Molecular Cloning—A Laboratory Manual (2nd Ed.), Vol. 1-3, Cold Spring Harbor Laboratory, Cold Spring Harbor, N.Y., 1989; Kriegler, Gene Transfer and Expression: A Laboratory Manual (1990); and Current Protocols in Molecular Biology (Ausubel et al., eds., 1994)).

Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise noted, technical terms are used according to conventional usage. Definitions of common terms in microbiology maybe found in e.g., Microbiology By Cliffs Notes, I. Edward Alcamo, Wiley (1996); Encyclopedia of Microbiology, (2000) supra; Singleton et al., Dictionary of Microbiology and Molecular Biology (2d ed. 1994). Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

B. Aflatoxins, Aflatoxin Contamination and Aflatoxigenic Fungi

Almonds, as well as most agricultural commodities, are known to have ambient microbes associated with them. Thus, they are endowed with a natural fungal bouquet. Of the fungal genera found during a study of the mycoflora of almonds, Apsergillus species figure prominently. As noted above, aflatoxins are mycotoxins produced by *Aspergillus flavus* and *A. parasiticus*, ubiquitous fungi of tree nut orchards (see e.g., Molyneux, R. J. et al. (2007) *Int. J. Food Microbiol*. 119: 72-78).

Aflatoxins represent a grave food safety problem due to their carcinogenic and teratogenic attributes (see e.g., Robens, J. and Cardwell, W. (2003) supra; Campbell, B. C.; et al. (2003) *J. Toxicol. Toxin Rev* 22: 225-266).

Tree nuts are typically sold and consumed as are consumed as whole nuts and undergo only minimal or very light processing, e.g., blanching, prior to sale. Typically, any subsequent processing, such as e.g., incorporation into baked goods is performed after aflatoxin analysis has been performed. There is thus little opportunity to reduce aflatoxin levels prior to sale. Therefore, to ensure that consumers as well as producer are protected from the worst consequences of aflatoxin contamination of tree nut crops, aflatoxin contamination must be detected early.

Fortunately, the methods disclosed herein are applicable to tree nut crops, as well as other aflatoxin contaminated crops e.g., cotton, peanuts, corn, etc.

III. Volatile Organic Compounds

A. Volatile Organic Compound (VOC) Sampling and Analysis

In an exemplary embodiment, volatile organic compounds (VOCs) indicative of aflatoxigenic aspergilli are reliably detected in the context of their natural environment (i.e., in the presence other fungal species in a natural fungal bouquet) using volatile emissions as an indicator. In an exemplary embodiment, tree nut crops or crop products, e.g., almonds, pistachios, etc, are subjected to analyses to determine if the composition and amount of the VOCs is indicative of the presence of aflatoxigenic aspergilli.

Any suitable method for sampling VOCs may be used. Exemplary sampling methods include, but are not limited to the use of sorbent sampling tubes e.g., charcoal tubes, Tenax tubes, SPME fibers and XAD2 tubes. Sorbent sampling is well known in the art (see e.g., ASTM D6196-03 Standard Practice for Selection of Sorbents, Sampling, and Thermal Desorption Analysis Procedures for Volatile Organic Compounds in Air; I. Ciucanu et al. (2003) *Anal. Chem*., 75 (4):736-741; Harper, M. (2000) Journal of Chromatography A 885 (1-2):129-151; EPA Method 5021A: *Volatile Organic Compounds in Various Sample Matrices Using Equilibrium Headspace Analysis*).

Sampled VOCs are then analyzed to determine whether profile is indicative of the presence of VOCs that are characteristically associated with the presence of aflatoxigenic aspergilli when those aspergilli are present in co-existent with other fungal species in their natural environment in a natural fungal bouquet. In some exemplary embodiments, the analytic/determinative method is carried out using an instrument, e.g., a gas chromatograph, and the analytic instrument is coupled to the sampling device. Exemplary analytical/determinative methods include, but are not limited to: gas chromatography (GC); gas chromatography-mass spectrometry (GC-MS) (see e.g., Beck, J. J.; et al. (2008) *J. Sci. Food. Agric*. 2008, 88, 1363-1368).

The skilled artisan, having access to this disclosure and the knowledge of the art, will recognize appropriate sampling and analytical methods for their particular experiment. Having chosen appropriate sampling and analytical methods the skilled artisan is prepared to sample VOCs on tree nut crops and/or tree nut crop products, to determine if the tree nut crop and/or tree nut crop product comprises aflatoxins and/or aflatoxigenic aspergilli. Any number of samples and any sampling interval can be used, provided that the number of samples and/or the sampling interval permit the skilled artisan to determine and detect, if present, volatile organic compounds (VOCs) characteristically associated with aflatoxins and/or aflatoxigenic aspergilli and thereby to be able to determine if the tree nut crop and/or tree nut crop product comprises aflatoxins and/or aflatoxigenic aspergilli.

In exemplary embodiments, the aflatoxigenic aspergilli are present as members comprising a natural fungal bouquet from almond hulls.

B. Volatile Emission Profile

Volatile organic compounds (VOCs) indicative of the presence of aflatoxins and/or aflatoxigenic aspergilli (i.e., "indicator volatiles") are separated from other VOCs using any method known in the art. Typically, identified and separated indicator volatiles provide an emissions profile that can be compared to a control volatile emission profile and which thereby can be used to determine whether or not aflatoxins and/or aflatoxigenic aspergilli are present in a tree nut crop. In one exemplary embodiment, the tree nut crop is an almond crop.

Exemplary identification/separation methods include, but are not limited to gas chromatography (GC), gas chromatography-mass spectrometry (GC-MS), high performance liquid chromatography (HPLC) all of which are well known in the art (see e.g., Lloyd R. Snyder and John W. Dolan (2006). *High-Performance Gradient Elution: The Practical Application of the Linear-Solvent-Strength Model*. Wiley Interscience; Message, Gordon M. (1984). *Practical aspects of gas chromatography/mass spectrometry*. New York: Wiley; Adlard, E. R.; Handley, Alan J. (2001). Gas chromatographic techniques and applications. London: Sheffield Academic).

In one exemplary embodiment, unique volatile indicators associated with the presence of aflatoxins in an almond crop include, but are not limited to (E)-2-nonenal, (E)-2-decenal and (E)-2-octenal.

In another exemplary embodiment, appearance of the unique volatile indicators (E)-2-nonenal, (E)-2-decenal and (E)-2-octenal is accompanied by increases in the amounts and or concentrations of hexanal, heptanal, octanal, 3-octen-2-one, nonanal, and decanal. In one exemplary embodiment, the amounts of hexanal, heptanal, octanal, 3-octen-2-one, nonanal, and decanal that accompany the appearance of the unique volatile indicators (E)-2-nonenal, (E)-2-decenal and (E)-2-octenal, are increased by at least about 200% in an aflatoxin contaminated tree nut crop as compared with an uncontaminated tree nut crop. In another exemplary embodiment, the amounts of hexanal, heptanal, octanal, 3-octen-2-one, nonanal, and decanal that accompany the appearance of the unique volatile indicators (E)-2-nonenal, (E)-2-decenal and (E)-2-octenal, are increased by at least about 250% in an aflatoxin contaminated tree nut crop as compared with an uncontaminated tree nut crop. In still another exemplary embodiment, the amounts of hexanal, heptanal, octanal, 3-octen-2-one, nonanal, and decanal that accompany the appearance of the unique volatile indicators (E)-2-nonenal, (E)-2-decenal and (E)-2-octenal, are increased by at least about 300% in an aflatoxin contaminated tree nut crop as compared with an uncontaminated tree nut crop. In still other exemplary embodiments, the amounts of hexanal, heptanal, octanal, 3-octen-2-one, nonanal, and decanal that accompany the appearance of the unique volatile indicators (E)-2-nonenal, (E)-2-decenal and (E)-2-octenal, are increased by at least about 350%, 400%, 450%, 500%, 550%, 650%, 750%, 850%, 950%, 1000% or more in an aflatoxin contaminated tree nut crop as compared with an uncontaminated tree nut crop.

The presence of aflatoxins may or may not indicate the presence of aflatoxigenic aspergilli. Indeed, in one exemplary embodiment, the volatile emissions profile from blanched almonds which have contacted aflatoxigenic aspergilli, but which have no detectable aflatoxigenic aspergilli present at the time of analysis, show increases in the amount of volatile indicators including increases in (E)-2-octenal, (E)-2-nonenal, and (E)-2-decenal by comparison to the amount of each of these volatile compounds comprising the volatile emission profile of blanched almonds known to be uncontaminated with aflatoxins and/or aflatoxigenic aspergilli. In another exemplary embodiment, the volatile emissions profile from blanched almonds which have contacted aflatoxigenic aspergilli, but which have no detectable aflatoxigenic aspergilli present at the time of analysis, show increases in the amount of volatile indicators including increases in hexanal, heptanal, octanal, (E)-2-octenal, 3-octen-2-one, nonanal, (E)-2-nonenal, decanal, and (E)-2-decenal by comparison to the amount of each of these volatile compounds comprising the volatile emission profile of blanched almonds known to be uncontaminated with aflatoxins and/or aflatoxigenic aspergilli.

III. Tree Nut Harvest

In one exemplary embodiment, harvested tree nut crops are analyzed for the presence of aflatoxins and/or aflatoxigenic aspergilli.

Tree nuts are typically harvested either by shaking, or by hand. In an exemplary embodiment, the tree nuts are almonds. In one exemplary embodiment, the almond trees are shaken to remove the almonds (which are in shell, but which have undergone hull split) from trees. Almonds (or other tree nuts) are dropped to the ground where they are allowed to dry, typically for about 2-3 days. Subsequently, dropped and dried almonds are swept into wind rows to await transfer to temporary holding containers; contained almonds are transported to stockpiles to await hulling. Environment Protection Agency (EPA) publication AP 42 CH. 9.10.2.1 discloses exemplary processes for harvesting almonds. In exemplary embodiment, tree nut crops are analyzed for aflatoxins at any or all of the stages of harvest and/or post harvest e.g., in wind-swept rows, in temporary holding containers, in stockpiles.

IV. Post Harvest Detection of Indicator Volatiles and Generation of a Volatile Emission Profile Under Field Conditions Instrumentation In an exemplary embodiment a volatile emission profile of field samples of a tree nut crop e.g., almond crops, is generated using a portable gas chromatography-mass spectrometer (GC-MS). Portable GC-MS instruments are known in the art (see e.g., U.S. Pat. No. 5,611,846; Crume, C. Environ. Test. Anal. 2001, 10 (3), 22-26; Eckenrode, B. A. *J. Am. Soc. Mass Spectrom.* 2001, 12 (6), 683-693; Frishman, G.; Tzanani, N.; Amirav, A. *Field Anal. Chem. Technol.* 2001, 5 (3), 107-115. Lu, C.; Zellers, E. T. *Anal. Chem.* 2001, 73 (14), 3449-3457. Overton, E. B.; Carney, K. R.; Rogues, N.; Dharmasena, H. P. *Field Anal. Chem. Technol.* 2001, 5 (1-2), 97-105. Jia, M.; Koziel, J.; Pawliszyn, J. *Field Anal. Chem. Technol.* 2000, 4 (2-3), 73-84. Bingham, S.; Medlar, J.; Kabir, A.; Shende, C.; Alli, A.; Malik, A. *Anal. Chem.* 2002, 74 (4), 752-761). However, any instrumentation suitable for generating a volatile emission profile maybe used in the methods disclosed herein.

Other exemplary instrumentation suitable for generating a volatile emission profile include, but are not limited to, proton-transfer reaction mass spectrometry (PTR-MS) (see e.g., Lindinger, W. et al. (1998) Int J Mass Spectrom Ion Proc 17333, 191-241; Karl, T.; Crutzen, P. J. et al. (2001) Atmos Environ 35:5287-5300; de Gouw, J.; Warneke, C. Mass Spectrom. Rev. (2007) 26, 223-257; Blake, R. S. et al. (2009) Chem. Rev. 109: 861-896); selected ion flow tube-Mass spectrometry (SIFT-MS); eNose (see e.g., Henderson, W. G.; et al. (2010). Comp Electronics Agric 70, 157-162); zNose (see e.g., Tholl, D.; et al. (2006) Plant J 45: 540-560; Kunert, M.; Biedermann, A.; Koch, T. Boland, W. J Sep Sci 2002 25 677-684).

Other suitable methods known in the art which are used for generating a volatile emission profile further include, TD-GC-IR-MS (see e.g Turner, N.; Jones, M.; Grice, K.; et al. Atmos Environ 2006, 40, 3381-3388); GC-FT-IR with an approximate LOD of ppt (see e.g Schrader, W.; Geiger, J.; et al. J Chromatog A 1999, 864, 299-314); GC-UV (ppm or less see e.g Nillson, A, Lagesson, V.; Bornehag, C.-G.; Sundell, J.; Tagesson, C. Environ Int. 2005, 31, 1141-1148); CG- NIR—(see e.g., Smyth, H. E.; Cozzolino, D.; et al. Anal Bioanal Chem 2008, 390, 1911-1916)

Detection of Indicator Volatiles and Generation of a Volatile Emission Profile

For the purpose of practicing the methods disclosed herein, any suitable instrument can be employed as long as the instrument can detect volatile organic compounds that are associated with aflatoxin contaminated tree nut crops. In one exemplary embodiment, the instrument detects the unique volatile indicators (E)-2-nonenal, (E)-2-decenal and (E)-2-octenal, which are indicative of aflatoxin contamination. In other exemplary embodiments, the instrument detects appearance of the unique volatile indicators (E)-2-nonenal, (E)-2-decenal and (E)-2-octenal in an aflatoxin contaminated tree nut crop and additionally detects increases of at least about 200% in the amounts and/or concentrations of hexanal, heptanal, octanal, 3-octen-2-one, nonanal, and decanal in the aflatoxin contaminated crop as compared to the amounts and/or concentrations of hexanal, heptanal, octanal, 3-octen-2-one, nonanal, and decanal in a uncontaminated control tree nut crop.

Figure 3:
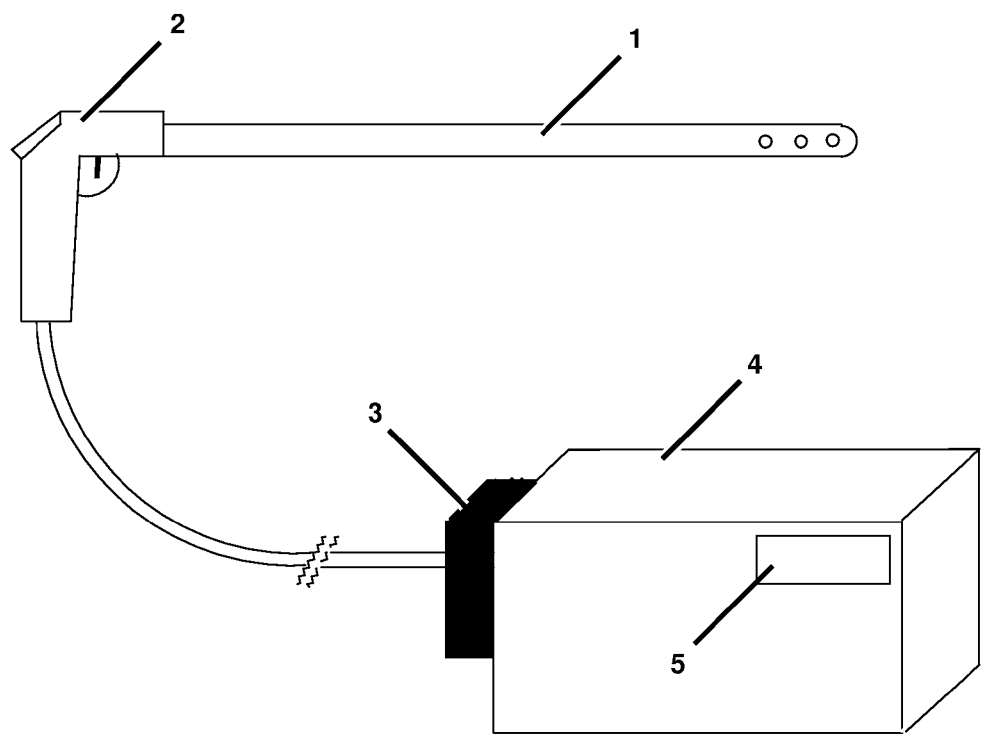
FIG. 3. Collection device for detecting indicator volatiles in-field. 1. Stainless steel tube (ca. 1 m) with holes at end for volatile collections; 2. Hand held trigger device with air flow controls, start and stop, and collection timer; 3. Pump for air flow from tube tip to collection device (cryo-cool, absorbent medium, etc.); 4. Portable GC-MS system for immediate injection of collected volatiles for separation, identification, and quantification; 5. Display of total-ion chromatogram (TIC) GC trace, and notification of indicator volatiles.
Figure 4:
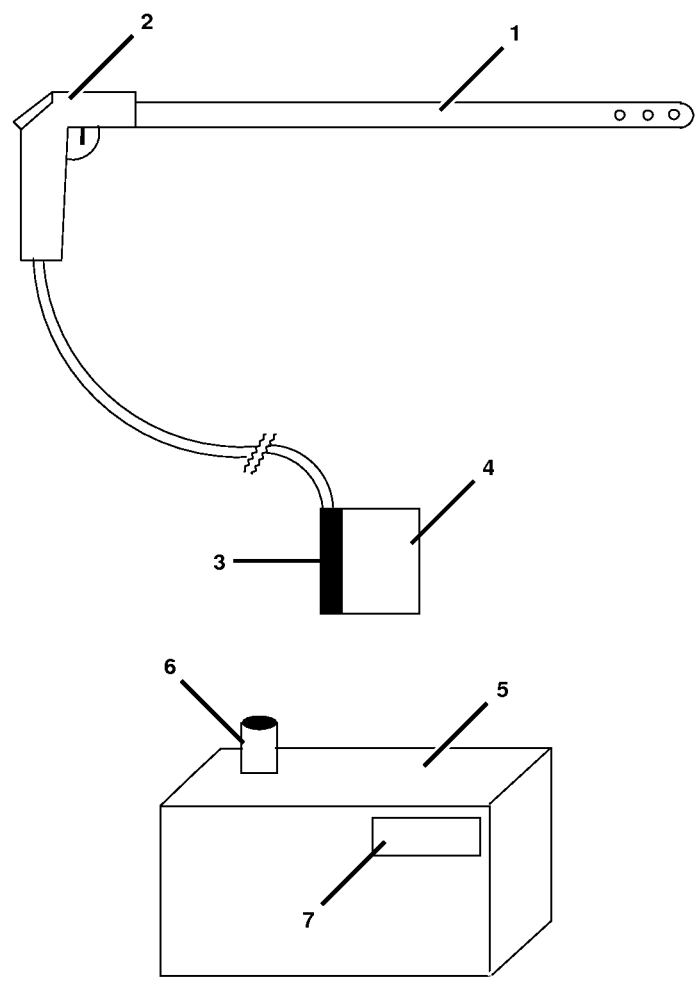
FIG. 4. Stainless steel tube (ca. 1 m) with holes at end for volatile collections; 2. Hand held trigger device with air flow controls, start and stop, and collection timer; 3. Battery-operated pump for air flow from tube tip to collection device; 4. Belt-worn portable collection tube holders. For each collection, tubes would be inserted/plugged into the hand-held device; the pump would pump volatiles onto the absorbent or adsorbent medium. After the sample collection was complete, a new tube would be inserted and ready for a new sample; 5. Portable, semi-portable, or bench-top GC-MS; 6. Tube holder for thermal desorption and injection into GC-MS; 7. Display of total-ion chromatogram (TIC) trace, and notification of indicator volatiles.

In some exemplary embodiments, a portable GC-MS instrument is used for field analysis. An exemplary portable GC-MS instrument for in field analysis is shown in FIG. 3. Another exemplary portable or semi portable GC-MS instrument for in field analysis is shown in FIG. 4. Typically, an exemplary device for in-field analysis comprises a 'probe' made from e.g., hollow stainless steel or aluminum material, which is attached to a device which allows for the drawing of air from the tip of the 'probe'. In an exemplary embodiment, the probe is inserted into a sample of tree nuts being tested. In exemplary embodiments, the sample of tree nuts being tested is an almond stockpile. In exemplary embodiments, the sample of tree nuts being tested is a wind-swept row or almonds in a storage or transit container.

In an exemplary embodiment, the pump of a portable GC-MS instrument such as e.g., that shown in FIG. 3, is trigger-activated, and air flow is at a set velocity for a set time to provide for a total volume that provides reproducibility across collection sites. In some exemplary embodiments once the trigger mechanism is activated, a timer starts. The timer alerts the user at time expiration and turns off automatically. A typical set time is chosen with an air flow velocity so as to collect sufficient volume of VOC's to detect the unique indicator volatiles (E)-2-nonenal, (E)-2-decenal and (E)-2-octenal. In other exemplary embodiments, a typical set time is chosen with an air flow velocity so as to collect sufficient volume of VOC's to detect the indicator volatiles (E)-2-nonenal, (E)-2-decenal and (E)-2-octenal, and also to detect appropriate increases in indicator volatiles hexanal, heptanal, octanal, 3-octen-2-one, nonanal, and decanal.

Typically air flow velocity is chosen to be in a range that is between about 50 mL/min and about 500 mL/min, although any suitable air flow velocity may be used. Thus, in some exemplary embodiments air flow velocity is 100 mL/min, 150 mL/min, 200 mL/min, 250 mL/min, 300 mL/min, 350 mL/min, 400 mL/min, 450 mL/min or any other convenient air velocity flow rate. Indeed, to practice the methods disclosed herein, the skilled practitioner will appreciate that the flow velocity of the sampled air should be such that an appropriate volume of air can be captured so as to be able to detect one or more indicator volatiles, if present, and to collect that volume in a convenient/reasonable period of time. As the skilled practitioner also appreciates, the air volume needed to be collected in order to detect indicator volatiles and thereby to provide a volatile emission profile, depends to a large extent on the sensitivity of the detection method/instrumentation being used for the particular analysis.

For example the limit of detection (LOD) for an indicator volatile using GC-MS for detection is about 0.1 part per trillion (ppt). The LOD for an indicator volatile using chemical ionization mass spectroscopy for detection is about 1-25 ppt (see e.g., Huey, L. G. Mass Spectrom. Rev. 2007, 26, 166-184). The LOD for an indicator volatile using SIFT-MS for detection is in the part per billion (ppb) range (see e.g., Freeman, C. G.; McEwan, J. J. Aust J Chem 2002, 55, 491-494); The LOD for an indicator volatile using PTR-MS is about 10-100 ppt (see e.g., Lindinger, W.; Nahsel, A.; Jordan, A. Int J Mass Spectrom Ion Proc 1998 17333, 191-241; Karl, T.; Crutzen, P. J.; Mandl, M.; et al. Atmos Environ 2001 35 5287-5300; de Gouw, J.; Warneke, C. Mass Spectrom. Rev. 2007, 26, 223-257; and Blake, R. S.; Monks, P. S.; Ellis, A. M. Chem. Rev. 2009, 109, 861-896) The LOD for an indicator volatile using eNose is in a range of ppm to ppb (see e.g., Henderson, W. G.; Khalilian, A.; Han, Y. J.; Greene, J. K.; Degenhardt, D. C. Comp Electronics Agric 2010 70, 157-162); The LOD for an indicator volatile using zNose is in the part per billion (ppb) range see e.g., Tholl, D.; Boland, W.; Hansel, A.; et al. Plant J 2006 45 540-560; Kunert, M.; Biedermann, A.; Koch, T. Boland, W. J Sep Sci 2002 25 677-684.

In one exemplary embodiment detectors are chosen to facilitate volatile detection of tree nut crops in the field. In one exemplary embodiment, a portable GC-MS detection system using a sorbent collector is used to collect VOCs. In an exemplary embodiment, sorbent captured volatiles are cryo-focused and condensed via cooling by methods known in the art (see e.g., Matsunaga et al., (2002) Atmos Environ 2002, 36, 6051-6057) and are subsequently injected onto GC-MS. In other exemplary embodiments, volatiles are collected by absorption onto a medium (e.g., Tenax® or Q-Pak®), and are thermally desorbed into GC-MS by methods known in the art (see e.g., Wilkes, et al. (2000) J Chromatog A 2000 880 3-33). In some exemplary embodiments the GC instrument is modified with a shortened column to facilitate detection of lower concentrations of volatiles. In another exemplary embodiment, the portable GC-MS is modified with a shortened column and a toroidal ion trap MS.

In some exemplary embodiments, a probe such as that illustrated in the portable device shown in FIG. 3 or FIG. 4 is used to pass the air flow comprising VOCs across a real-time detector e.g., an e-nose (see e.g., W. G. Henderson et al. (2010) Computers and Electronics in Agriculture 70 (2010) 157-162) or z-nose (see e.g., M. Kunert et al (2002) J. Sep. Sci. 25, 677-684) detector. Thus, in some exemplary embodiments, volatile organic compounds indicative of aflatoxins are detected in "real-time".

In some exemplary embodiments, eNose or zNose technology is used in-field to detect and analyze VOCs indicative of aflatoxin contamination of tree nut crops e.g., almond, crops in "real-time". E-nose technology is known in the art (see e.g., Henderson, W. G.; et al. (2010)). In an exemplary embodiment, eNose detectors are pre-sensitized to detect (E)-2-octenal, (E)-2-nonenal, and (E)-2-decenal. Concentration of (E)-2-octenal, (E)-2-nonenal, and (E)-2-decenal in field samples are compared to samples taken from an uncontaminated control. The appearance of one or more of the unique volatile indicators (E)-2-nonenal, (E)-2-decenal and/or (E)-2-octenal, is indicative of aflatoxin contamination. In some exemplary embodiments, e-nose detectors are pre-sensitized to detect in addition to the unique volatile indicators (E)-2-nonenal, (E)-2-decenal and (E)-2-octenal, hexanal, heptanal, octanal, 3-octen-2-one, nonanal, and decanal. In these exemplary embodiments, the appearance of any one or more of the unique volatile indicators (E)-2-nonenal, (E)-2-decenal and (E)-2-octenal, and appropriate increases (see above) in hexanal, heptanal, octanal, 3-octen-2-one, nonanal, and decanal, is indicative of aflatoxin contamination.

zNose technology is also known in the (see e.g., Tholl, D.; et al. (2006) supra; Kunert, M.; et al. supra). In an exemplary embodiment, zNose detectors are pre-sensitized to detect the unique volatile indicators (E)-2-octenal, (E)-2-nonenal, and (E)-2-decenal. The amount and/or concentration of any one or more of (E)-2-octenal, (E)-2-nonenal, and (E)-2-decenal in field samples are compared to the amount and/or concentration of these unique indicator volatiles in samples taken from an uncontaminated control. The appearance of one or more of the unique volatile indicators (E)-2-nonenal, (E)-2-decenal and/or (E)-2-octenal, is indicative of aflatoxin contamination. In other exemplary embodiments, z-nose detectors are pre-sensitized to detect, in addition to the unique volatile indicators (E)-2-octenal, (E)-2-nonenal, and (E)-2-decenal, hexanal, heptanal, octanal, (E)-2-octenal, 3-octen-2-one, nonanal, (E)-2-nonenal, decanal, and (E)-2-decenal. In these exemplary embodiments, the appearance of any one or more of the unique volatile indicators (E)-2-nonenal, (E)-2-decenal and (E)-2-octenal, and appropriate increases (see above) in hexanal, heptanal, octanal, 3-octen-2-one, nonanal, and decanal, is indicative of aflatoxin contamination.

In other exemplary embodiments, Selected Ion Flow Tube Mass Spectrometry (SIFT-MS) is used for "real-time" detection in-field detection and analysis of VOCs indicative of aflatoxin contamination of tree nut e.g., almond, crops. SIFT-MS is known in the art (see e.g., Smith D, and Spanel P. (2005) *Mass Spectrom Rev.* 24(5):661-700).

In still other exemplary embodiments, Proton-transfer reaction mass spectrometry PTR-MS, is used for "real-time" detection in-field detection and analysis of VOCs indicative of aflatoxin contamination of tree nut e.g., almond, crops. PTR-MS is known in the art (see e.g., Lindinger, W. et al. (1998) Int J Mass Spectrom Ion Proc 17333, 191-241; Karl, T.; Crutzen, P. J. et al. (2001) Atmos Environ 35:5287-5300; de Gouw, J.; Warneke, C. Mass Spectrom. Rev. (2007) 26, 223-257; Blake, R. S. et al. (2009) Chem. Rev. 109: 861-896).

Detection of Indicator Volatiles In Wind-Swept Rows

In an exemplary embodiment, aflatoxins are detected on tree nut crops e.g., almonds when the aflatoxins and aflatoxigenic fungi are co-existent with other fungi in a natural fungal bouquet.

In an exemplary embodiment, z-nose technology is used to detect indicator volatiles wind-swept almond rows. In this embodiment, a probe such as e.g., that associated the instrument illustrated in FIG. 3, or any other suitable means of delivering air samples from a wind-swept row to a zNose detector, is waved above and/or within the wind-swept row to collect air samples and detect indicator volatiles if present.

In another exemplary embodiment, eNose technology is used to detect indicator volatiles wind-swept almond rows. In this embodiment, a probe such as e.g., that associated the instrument illustrated in FIG. 3, or any other suitable means of delivering air samples from a wind-swept row to the e-nose detector, is waved above and/or within the wind-swept row to collect air samples and detect indicator volatiles if present. A region or regions of the wind-swept rows having indicator volatiles present could be removed prior to further processing of the almonds. In one exemplary embodiment, the almond wind-swept rows are swept over with a hand-held, or ATV-mounted, or equipment mounted e-nose to scan awaiting almonds for increased VOC emissions indicative of aflatoxin contamination.

In other exemplary embodiments, almonds are placed on a conveyor belt and an e-nose or z-nose detector is swept above the almonds as they pass by. If volatile organic compounds (VOCs) indicative of aflatoxin contamination (indicator volatiles) e.g., the appearance of the unique indicator volatiles (E)-2-nonenal, (E)-2-decenal and (E)-2-octenal are detected, the contaminated batch can be identified, and discarded if desired.

Detection of Indicator Volatiles In Storage and/or Shipment Containers

In one exemplary embodiment, harvested tree nut crops are analyzed for the presence of aflatoxins and/or aflatoxigenic aspergilli while in storage and/or shipment containers.

For purposes of practicing the methods disclosed herein and their equivalents, a storage and/or shipping container refers to a enclosure (sealed or unsealed) which is capable of storing post harvest tree nuts e.g., almonds, walnuts, pistachios, etc. In some exemplary embodiments, a storage and/or shipping container is capable of generating and maintaining a controlled atmosphere. The nature of the enclosure is not important, all that is needed is an enclosure in which the internal atmospheric conditions can be monitored. For example the enclosure may be any enclosure known e.g., a box, a sphere, a room, a truck, a trailer, a semitrailer, a boat, a barge, a railroad car, an aircraft, any imaginable enclosure that provides an enclosed space wherein the atmosphere inside the enclosure can be monitored for VOC levels.

In sampling VOCs in a shipping or storage container VOCs are typically collected and concentrated prior to injection onto a gas chromatograph. Indeed, in some exemplary embodiments, VOCs in a shipping or storage container the concentration of target analytes is below the detection limit of a particular analytical technique. A wide range of concentrations may be present, for instance from 1 ppmV (1 part per million by volume) down to 1 pptV—a range of one million. Two concentration methods are commonly employed: (a) cryogenic focusing/concentration and (b) adsorbent focusing/concentration. In each method an air sample of the desired volume is passed through an accumulation chamber, which consists of: (a) a 'U-tube' immersed in a cryogenic liquid, such as liquid oxygen or air, or which is otherwise cooled sufficiently that some or all of the target analytes condense to liquids or solids within the U-tube trap, also referred to herein as a cryotrap. Most of the air sample does not condense and therefore passes through the trap; or (b) a sorbent-filled trap, which absorbs or adsorbs some or all of the target analytes, allowing most of the sample to pass through. Such traps can operate at ambient temperature or below. Either procedure concentrates the desired analytes to a concentration much higher than their original concentration in the air sample. After the desired air volume has passed through the trap, yielding sufficient analyte, the trap is heated to transfer the concentrated analytes into a chromatographic column or other analytical device. Thus, in an exemplary embodiment cryogenic focusing/concentration is used to concentrate volatiles present in a shipping or storage container for analysis. In other exemplary embodiments, adsorbent focusing concentration is used to concentrate volatiles present in a shipping or storage container for analysis.

In another exemplary embodiment, pneumatic focusing and a device such as that disclosed in U.S. Pat. No. 7,257,987, which is incorporated herein by reference, is used to concentrate and measure VOCs in shipping and storage container and hence is used to provide a volatile emission profile characteristic of the entire container of a particular tree nut crop in that container.

In another exemplary embodiment, a fixed absorptive/adsorptive medium e.g., Tenax®, Q-Pak®, SPME, PDMS that container air, and subsequent VOC emission, is periodically passed across for ab/adsorption. Captured VOCs are then thermally desorbed into a detector (e.g., EI-MS, SIFT-MS, UV, NIR, IR, FL) and compared against the initial VOC output of a non-contaminated control. If any one or more of the unique volatile indicators (E)-2-octenal, (E)-2-nonenal, and (E)-2-decenal are detected, and/or if there is an increase (by comparison with an uncontaminated control) in the concentration and/or amount of the indicator volatiles hexanal, heptanal, octanal, (E)-2-octenal, 3-octen-2-one, nonanal, and decanal, beyond a certain percentage e.g., 250% increase compared to a non-contaminated control, or any one or more of the unique volatiles become detectable, e.g., 2-(E)-decenal, a monitor notes the time and day. In some exemplary embodiments a container is remote and accessories such as interne capabilities alert pre-determined personnel of the change in VOC output, moisture content in container, and temperature cycles within the container. In a exemplary embodiment, a container which has been identified as contaminated would be further examined using a portable monitoring device such as that shown e.g., in FIG. 3 to locate that specific portion or portions of the bin's holdings that have developed a contamination hot spot. Thus, in an exemplary embodiment, the hand-held device comprising a probe is used to determine where the hot spot is. The contaminated hot spot can then be removed and the remaining shipment can be approved instead of losing the bin's entire contents.

The following examples are offered to illustrate, but not to limit the invention.

EXAMPLES

Example 1

The following example illustrates analysis of volatile output and correlation with aflatoxin content of almonds in their native processed state with their typical fungal bouquets intact Materials and Methods for Example 1

Almond Material

Twenty one batches of almonds, were provided by the Almond Board of California from random processors throughout the California Central valley and chosen as 'pick-outs'—almonds with an increased probability of aflatoxin contamination. Portions of the collected almonds underwent commercial processing and mimicked that of stored whole almonds ready for transit (samples 1, 2, 4, 5, 8, 9, 12, 13, 15, 17-21; volatiles listed in Table 1). A smaller set of whole almonds (samples 3, 6, 7, 10, 11, 14, and 16; volatiles listed in Table 2) underwent blanching during processing. Portions of each batch were ground as per homogeneity regulations for almond aflatoxin analyses by methods known in the art (see e.g., Commission Regulation (EC) No 401/2006. *Official J. Eur. Union* 2006, L70/12-L7034). Both whole and ground almonds were placed in separate sealed containers, stored at −10° C., and warmed to room temperature prior to analyses.

Almond Fungal Volatile Collections

Ground samples (6 g) were removed from random locations from storage containers and placed in a 25 mL Erlenmeyer flask and sealed with a screw cap containing a Telfon port using methods known in the art (see e.g., J. J. Beck, et al. (2008) *J. Agric. Food Chem.* 56:11392-11398). Once sealed, the volatiles were adsorbed onto a SPME (PDMS) using the P.E.S.T. parameters P=5 min; E=1 h; S=1 min; T=5 min (39).

Volatile Analyses

All experiments utilized transfer of adsorbed volatiles onto either a J&W Scientific (Folsom, Calif.) DB-Wax column (60 m×0.32 mm i.d.×0.25 µm), or a J&W Scientific DB-1 column (60 m×0.32 mm i.d.×0.25 µm) installed on one of two HP-6890 gas chromatographs (GC) coupled to HP-5973 mass selective detectors (MS, Palo Alto, Calif.). Desorbed volatiles were analyzed with the methods previously reported (40), but with the following change in program: ramp one, 4° C./min; final temp, 180° C.; hold time, 0.0 min; post-run 210° C.; hold time, 5.0 min. NIST, Wiley, and internally generated databases were used for fragmentation pattern identification. The retention indices (RIs) were calculated using a homologous series of n-alkanes on the DB-Wax and DB-1 columns. Volatile identifications were verified by injection of authentic samples and comparison to retention times of an internally-generated list of volatiles on identical columns.

Colony Forming Unit (CFU) Counts of *A. flavus* and *A. parasiticus*

The CFU counts on the ground almonds were performed via the following method: inedible almond samples were hand sorted to remove hulls, rocks, twigs, and other typical field contaminants. Each almond kernel sample (1 kg) was ground to a fine consistency using a food processor with the nut grater attachment (Electrolux). *A. flavus* and *A. parasiticus* agar (AFPA) was prepared per literature protocol (41) and from the following components: Bacto yeast extract (BD), 20 g/L; Bacto peptone (BD), 10 g/L; ferric ammonium citrate (Sigma), 0.5 g/L; dichloran (Sigma), 1 mL of a 0.2% solution in ethanol; Bacto agar (BD), 15 g/L; chloramphenicol (Sigma) 0.1 g/L. Fungal counts were measured in triplicate for each almond sample. Ground almond (40 g) was added to maximum recovery diluent (200 mL, Oxoid), stirred for 30 min, followed by aliquot dilutions of 1:10, 1:20, and 1:40 (v/v). An aliquot from each dilution (0.1 mL) was spread on an AFPA Petri dish and incubated at 30° C. Total fungal colonies and colonies of *A. flavus* and *A. parasiticus* showing orange pigmentation on the reverse were counted after 42-48 h.

Aflatoxin Standards and Analyses

Aflatoxin standards were prepared as per AOAC 971.22 (18th edition, 2005) and previously published methods (see e.g., N. Mahoney, and Molyneux, R. J. (2010) *J. Agric. Food Chem.* 58:4065-4070). Upon completion of volatile collection, each sample was subjected to aflatoxin analysis using a method similar to previously published protocols (42). Ground almond kernels (6 g) were blended in an MC3 mini container (Waring) with methanol/water (60:40, 25 mL) and NaCl (1 g) for 1 min. The mixture was gravity filtered through fluted filter paper (Whatman 2V) followed by syringe filtration (Pall 0.45 t nylon, 13 mm diameter) of a 2.5 mL portion. An aliquot (1.0 mL) of the extract was diluted with an equal volume of water and passed through an Aflatest P affinity column (Vicam) followed by a water wash (2 mL). Aflatoxins were eluted from the column with acetonitrile (2 mL), and the eluate evaporated to dryness under a stream of nitrogen at 40° C. The dried sample was dissolved in methanol (1.0 mL) and analyzed for aflatoxins by reversed phase HPLC (Agilent 1100, Santa Clara, Calif.). Conditions for HPLC analyses (Inertsil ODS-3, 4.6×250 mm): mobile phase water/acetonitrile/methanol (45:25:30); flow, 1.0 ml/min; temperature, 25° C.; detector, fluorescence, 365 nm excitation, 455 nm emission; derivatization, photochemical reactor (PHRED, Aura Industries), 25 m×0.25 mm ID coil; injection volume, 20 µL; retention times, G2—7.8 min, G1—8.7 min, B2—9.4 min, B1—10.6 min. All volatile, CFU, and aflatoxin experiments were performed in triplicate (n=3). All graphs, triplicate averages, standard deviations, and linear regression analyses were calculated using Excel (Microsoft Inc.).

Results for Example 1

The volatile analysis of ground almond samples provided a total of 33 compounds (Table 1 and 2) from 21 almond samples. There were no detectable sesquiterpenes in the present analysis.

Comparisons of the relative abundances of the 33 volatiles from random samples showed increases in select volatile compounds when samples containing zero amounts of AFG1 and AFG2 were compared to samples containing known amounts of AFG1 and/or AFG2. For example, the average amounts of the volatiles from sample 5 (5A, 5B, and 5C), which contained zero amounts of AFG1 and AFG2 were compared to the average amounts of the volatiles from sample 6, which contained AFG1 (1.8 ppb) and AFG2 (0.3 ppb). The volatiles hexanal, heptanal, octanal, nonanal, 3-octen-2-one, acetic acid, decanal, and hexanoic acid showed a marked increase in relative amounts in sample 6 as compared to sample 5.

Figure 2:
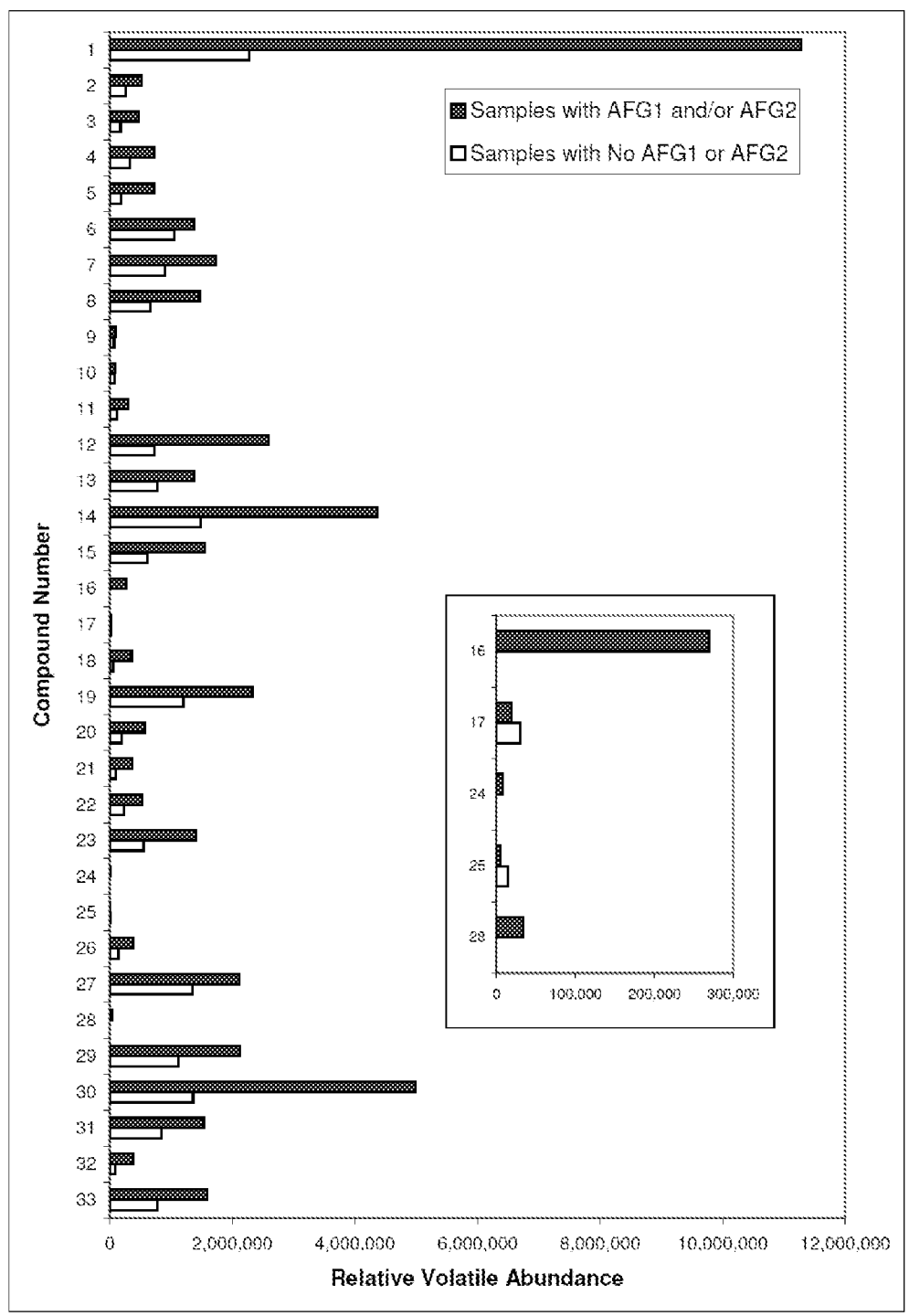

Next, the average of the 33 volatiles from all samples with zero ppb of AFG1 and AFG2 (1A, 1C, 4C, 5A-C, 7B, 8A, 8C, 12B, 12C, 14C, 15C, 17C, 19B, 19C, 20C, 21A, 21C) was compared to the average of the 33 volatiles from the remaining 44 samples containing some amount of AFG1 or AFG2 and the resultant graph in FIG. 2 was obtained. As is shown in FIG. 2, fourteen volatiles, namely compounds 1, 3, 5, 11, 12, 14, 15, 18, 20, 21, 23, 26, 30, and 32 increased by greater than 250% in samples containing some amount of AFG1 and/or AFG2 relative to the samples with no AFG1 and AFG2.

Three compounds, (E)-2-octenal (compound 16), (E)-2-nonenal (compound 24), and (E)-2-decenal (compound 28), were unique to the samples containing AFG1 and/or AFG2.

Linear regression analyses were performed on the individual volatile components from the 63 samples and evaluated relative to the AFG1, AFG2, AFB1, and AFG2 content

TABLE 1

All volatiles collected with their respective retention times, corresponding retention indices (based on n-alkanes) on two different columns (DB-1 polar, DB-Wax non-polar). Major identifying fragmentation ions are listed for both columns to show congruity between columns.

| | | DB-Wax RT | | DB-Wax | | DB-1 | DB-1 | | DB-Wax Auth. | DB-1 Auth. |
|---|---|---|---|---|---|---|---|---|---|---|
| PK | Library/ID | GAVA | Auth. | calc'd | Lit | RT Auth. | calc'd | Lit | Frag | Frag |
| 1 | hexanal | 6.52 | 6.53 | 1077 | 1077 | 6.30 | | 772 | 56, 44, 72, 82 | 56, 44, 72, 82 |
| 2 | undecane | 6.94 | 6.96 | 1098 | 1100 | 16.94 | 1097 | 1100 | 57, 43, 71, 85, 156 | 57, 43, 71, 85, 156 |
| 3 | 2-butyl furan | 7.75 | 7.76 | 1126 | 1126 | 9.21 | 878 | 877 | 81, 124, 53, 41, 95 | 81, 124, 53, 41, 95 |
| 4 | 2-heptanone | 9.05 | 9.07 | 1178 | 1178 | 8.86 | 867 | 865 | 43, 58, 71, 114, 99, 85 | 43, 5811, 114, 99 |
| 5 | heptanal | 9.12 | 9.12 | 1181 | 1180 | 9.13 | 875 | 876 | 70, 44, 55, 81, 96 | 70, 41, 55, 81, 96 |
| 6 | limonene | 9.50 | 9.54 | 1195 | 1197 | 14.10 | 1020 | 1020 | 68, 93, 79, 121, 136 | 68, 93, 79, 121, 136 |
| 7 | dodecane | 9.58 | 9.60 | 1198 | 1200 | 20.49 | 1197 | 1200 | 57, 43, 71, 85 | 57, 71, 43, 85 |
| 8 | 2-pentyl furan | 10.47 | 10.49 | 1228 | 1226 | 12.56 | 977 | 977 | 81, 138, 53, 95, 41, 67 | 81, 138, 53, 95, 41, 67 |
| 9 | ethyl hexanoate | 10.58 | 10.61 | 1232 | 1229 | 12.68 | 981 | 981 | 88, 99, 43, 60, 73, 115 | 88, 99, 43, 60, 73, 115 |
| 10 | p-cymene | 11.59 | 11.60 | 1266 | 1264 | 13.73 | 1009 | 1010 | 119, 134, 91, 77, 65 | 119, 134, 91, 77, 65 |
| 11 | 2-octanone | 12.07 | 12.06 | 1282 | 1281 | 12.13 | 966 | 967 | 43, 58, 71, 128, 85 | 43, 58, 71, 128, 85 |
| 12 | octanal | 12.18 | 12.18 | 1285 | 1284 | 12.55 | 977 | 979 | 41, 57, 84, 69, 100, 110 | 41, 57, 84, 69, 100, 110 |
| 13 | 1-hexanol | 14.30 | 14.29 | 1354 | 1350 | 8.29 | 848 | 848 | 56, 43, 41, 69, 84 | 56, 43, 69, 41, 84 |
| 14 | nonanal | 15.42 | 15.42 | 1390 | 1389 | 16.23 | 1079 | 1082 | 57, 41, 98, 70, 82, 114 | 57, 41, 98, 70, 82, 114 |
| 15 | 3-octen-2-one | 15.83 | 15.84 | 1404 | 1404 | 13.74 | 1009 | 1013 | 55, 111, 43, 97, 69, 126 | 55, 111, 43, 97, 69, 126 |
| 16 | (E)-2-octenal | 16.48 | 16.48 | 1425 | 1425 | 14.39 | 1029 | 1030 | 70, 55, 41, 83, 97, 108 | 70, 55, 41, 83, 97, 108 |
| 17 | ethyl octanoate | 16.76 | 16.76 | 1434 | 1432 | 19.76 | 1178 | 1180 | 88, 101, 127, 57, 73, 41 | 88, 101, 127, 57, 73, 41 |
| 18 | 1-octen-3-ol | 17.29 | 17.28 | 1451 | 1448 | 11.95 | 961 | 962 | 57, 72, 85, 99, 110 | 57, 72, 85, 99 |
| 19 | acetic acid | 17.41 | 17.11 | 1455 | 1475 | 3.53 | | 580 | 43, 45, 60 | 43, 45, 60, 42 |
| 20 | 1-heptanol | 17.47 | 17.47 | 1457 | 1454 | 11.60 | 951 | 951 | 70, 56, 83, 98 | 70, 56, 83, 98 |
| 21 | tetramethylpyrazine | 18.00 | 17.99 | 1474 | 1476 | 15.47 | 1059 | 1061 | 136, 54, 42, 95, 80, 121 | 136, 54, 42, 95, 121, 80 |
| 22 | 2-decanone | 18.51 | 18.51 | 1491 | 1491 | 19.49 | 1171 | 1172 | 58, 43, 71, 156, 85, 96 | 58, 43, 71, 156, 96, 85 |
| 23 | decanal | 18.65 | 18.64 | 1495 | 1495 | 19.89 | 1181 | 1184 | 57, 41, 82, 71, 95, 112 | 57, 41, 70, 82, 112, 95 |
| 24 | (E)-2-nonenal | 19.71 | 19.72 | 1531 | 1532 | 18.13 | 1132 | 1134 | 70, 41, 55, 83, 96, 111 | 70, 55, 83, 41, 96, 111 |
| 25 | ethyl nonanoate | 19.84 | 19.86 | 1535 | 1534 | 23.20 | 1277 | 1279 | 88, 101, 141, 73, 41, 55 | 88, 101, 141, 73, 55, 41 |
| 26 | 1-octanol | 20.58 | 20.58 | 1560 | 1558 | 15.23 | 1053 | 1053 | 56, 41, 69, 84, 97 | 56, 69, 41, 84, 97 |
| 27 | butyrolactone | 22.29 | 22.31 | 1618 | 1623 | 8.56 | 857 | 855 | 42, 41, 86, 56, | 42, 86, 56, 41 |
| 28 | (E)-2-decenal | 22.88 | 22.88 | 1639 | 1641 | 21.71 | 1234 | 1236 | 70, 55, 41, 83, 98, 110 | 70, 55, 41, 83, 98, 110 |
| 29 | γ-hexanolactone | 24.40 | 24.43 | 1692 | 1699 | 13.39 | 999 | 1003 | 85, 57, 42, 70, 114 | 85, 57, 42, 70, 114 |
| 30 | hexanoic acid | 28.75 | 28.51 | 1855 | 1825/1874 | 12, 37 | 972 | nd | 60, 73, 41, 87, | 60, 73, 41, 87, |
| 31 | γ-octanolactone | 30.15 | 30.15 | 1907 | 1916 | 20.80 | 1206 | 1210 | 85, 56, 57, 41, 100 | 85, 56, 57, 41, 100, 69 |
| 32 | phenol | 32.48 | 32.48 | 2002 | 2000 | 11.81 | 957 | 957 | 94, 66, 65, 40, 55 | 94, 66, 65, 40, 55, |
| 33 | γ-nonanolactone | 32.96 | 32.96 | 2022 | 2030 | 24.37 | 1311 | 1315 | 85, 41, 55, 56, 100, | 85, 55, 41, 56, 100, 70 | for each of the corresponding samples. (E)-2-octenal showed correlation ($R^2=0.18$) to AFG2 relative to the other compounds (average $R^2$ value of 0.06) to AFG2.

Attention was next shifted to segregation of data for the blanched and non-blanched analyses.

The blanched almond data in Table 2, when taken separately from the non-blanched data, show an overall increase in correlative information between the individual volatile amounts and aflatoxin content data. Indeed, the volatile (E)-2-decenal showed the highest correlation to AFG2 and AFG1, with $R^2$ values of 0.65 and 0.66, respectively. Correlations to AFB1 and AFB2 were generally much lower with $R^2$ values of about 0.20. Interestingly, other individual volatiles that demonstrated modest $R^2$ values, albeit lower compared to (E)-2-decenal, could be combined with (E)-2-decenal and to produce good correlations to aflatoxin content. For example, the combination of (E)-2-decenal and 1-octen-1-ol provided $R^2$ values of 0.48 to AFG1 and 0.49 to AFG2.

Further segregation of the blanched samples to include only those with no aspergilli CFUs (samples 7, 11, 14, and 16) and subsequent analysis provided higher correlation of the volatile combination (E)-2-decenal and 1-octen-1-ol to all aflatoxins present with $R^2$ values of 0.62 to AFG1, 0.62 to AFG2, 0.67 to AFB1, and 0.66 to AFB2. Interestingly, the blanched almonds exhibited VOC and aflatoxin presence; however, the fungal count was either extremely low or non-existent. This suggests the blanching process does eliminate and/or diminish fungal contamination, but does not eliminate any aflatoxin presence previously established by the aflatoxigenic aspergilli.

| PK | Library/ ID | DB-Wax[b] calc'd | Llt | Source | \multicolumn{7}{c}{Sample Number Relative Abundance[a]} | | | | | | |
|---|---|---|---|---|---|---|---|---|---|---|---|
| | | | | | 3 | 6 | 7 | 10 | 11 | 14 | 16 |
| 1 | hexanal[c] | 1077 | 1077 | | 5,860,857 (2,263,056) | 9,138,521 (6,084,403) | 767,950 (511,857) | 17,441,248 (7,831,816) | 21,725,538 (11,780,715) | 13,885,560 (5,820,917) | 5,244,908 (1,751,337) |
| 2 | undecane[d] | 1098 | 1100 | | 890,400 (374,790) | 170,905 (209,112) | 250,187 (147,248) | 328,579 (202,361) | 404,004 (215,914) | 229,453 (163,141) | 210,080 (159,445) |
| 3 | 2-butyl furan[c] | 1126 | 1126 | | 255,824 109,761 | 191,755 (149,930) | 32,624 (46,137) | 559,189 (332,185) | 702,686 (532,096) | 561,063 (276,626) | 263,914 (116,143) |
| 4 | 2-heptanone[c] | 1178 | 1178 | | 463,122 (196,345) | 342,854 (194,317) | 181,296 (115,891) | 842,627 (457,911) | 841,549 (506,691) | 766,374 (346,389) | 418,061 (190,158) |
| 5 | heptanal[d] | 1181 | 1180 | | 424,713 (182,562) | 527,804 (367,230) | 48,062 (51,032) | 1,023,027 (531,838) | 1,186,084 (714,313) | 1,072,037 (529,148) | 393,257 (171,721) |
| 6 | limonene | 1195 | 1197 | | 725,460 (337,051) | 635,428 (449,209) | 1,167,219 (605,750) | 810,997 (425,814) | 979,258 (495,800) | 739,733 (345,741) | 650,396 (336,658) |
| 7 | dodecane[d] | 1198 | 1200 | | 1,266,127 (520,929) | 283,713 (312,516) | 345,169 (206,581) | 2,039,813 (975,649) | 862,165 (549,749) | 2,665,906 (1,653,170) | 2,976,420 (1,502,497) |
| 8 | 2-pentyl furan[c] | 1228 | 1226 | | 1,084,131 (465,990) | 573,196 (418,003) | 261,589 (170,514) | 1,791,176 (973,866) | 1,540,374 (973,687) | 1,524,770 (785,988) | 814,319 (402,776) |
| 9 | ethyl hexanoate | 1232 | 1229 | | 0 | 0 | 29,273 (50,702) | 106,343 (99,041) | 91,852 (84,469) | 221,480 (210,939) | 39,925 (69,152) |
| 10 | p-cymene | 1266 | 1264 | | 33,544 (58,100) | 41,929 (72,623) | 55,181 (95,576) | 0 | 114,558 (100,625) | 0 | 44,692 (77,876) |
| 11 | 2-octanone[d] | 1282 | 1281 | | 271,959 (138,872) | 137,090 (149,551) | 0 | 320,064 (190,577) | 355,611 (207,620) | 383,649 (203,792) | 160,662 (109,217) |
| 12 | octanal[c] | 1285 | 1284 | | 1,496,340 (619,071) | 1,701,341 (1,113,405) | 238,929 (161,368) | 3,970,322 (2,110,538) | 3,958,359 (2,245,350) | 4,084,788 (1,807,648) | 1,308,246 (572,782) |
| 13 | 1-hexanol | 1354 | 1350 | | 418,057 (194,482) | 232,681 (256,054) | 3,364,826 (3,436,998) | 754,940 (437,834) | 811,721 (471,447) | 581,341 (390,199) | 918,101 (502,631) |
| 14 | nonanal[c] | 1390 | 1389 | | 2,658,172 (977,431) | 2,941,740 (1,936,281) | 481,356 (251,938) | 6,030,191 (3,208,605) | 5,757,940 (3,353,698) | 6,445,689 (3,049,052) | 2,726,110 (1,300,648) |
| 15 | 3-octen-2-one[d] | 1404 | 1404 | | 826,894 (345,014) | 1,025,248 (681,221) | 153,103 (138,588) | 2,054,605 (1,130,736) | 2,374,791 (1,406,931) | 1,954,546 (955,918) | 942,731 (482,574) |
| 16 | (E)-2-octenal | 1425 | 1425 | | 72,763 (126,030) | 204,841 (229,148) | 0 | 579,373 (330,205) | 645,421 (415,090) | 81,528 (141,211) | 0 |
| 17 | ethyl octanoate | 1434 | 1432 | | 0 | 0 | 0 | 0 | 0 | 108,323 (93,818) | 0 |
| 18 | t-octen-3-ol[d] | 1451 | 1448 | | 140,522 (71,193) | 308,681 (210,245) | 0 | 588,675 (339,001) | 1,157,751 (931,282) | 335,447 (230,560) | 198,230 (97,969) |
| 19 | acetic acid | 1455 | 1475 | | 1,755,000 (2,380,6561) | 793,333 (527,857) | 676,667 (601,360) | 1,950,000 (1,603,901) | 3,351,049 (1,604,405) | 3,027,329 (2,035,060) | 2,233,333 (642,910) |
| 20 | heptanol | 1457 | 1454 | | 0 | 0 | 446,134 (452,143) | 505,767 (876,014) | 1,424,643 (1,233,940) | 1,899,172 (653,993) | 0 |
| 21 | tetramethyl pyrazine[d] | 1474 | 1476 | | 550,478 (226,965) | 283,850 (140,681) | 116,132 (100,587) | 406,135 (236,920) | 605,097 (332,602) | 301,118 (151,518) | 300,084 (138,913) |
| 22 | 2-decanone[d] | 1491 | 1491 | | 228,796 (105,420) | 272,718 (197,144) | 0 | 585,455 (312,760) | 726,516 (433,396) | 967,717 (471,966) | 512,613 (272,5138) |
| 23 | decanal[d] | 1495 | 1495 | | 840,266 (324,285) | 764,029 (593,848) | 224,412 (148,863) | 2,044,545 (1,119,788) | 2,028,489 (1,220,464) | 2,598,349 (1,315,265) | 685,513 (348,955) |
| 24 | {E}-2-nonenal | 1531 | 1532 | | 0 | 56,393 (97,575) | 0 | 0 | 0 | 0 | 0 |
| 25 | ethyl nonanoate | 1535 | 1534 | | 0 | 0 | 0 | 0 | 0 | 0 | 0 |
| 26 | t-octanol | 1560 | 1558 | | 0 | 42,441 (73,510) | 550,918 (686,845) | 204,251 (234,243) | 994,742 (661,606) | 901,580 (460,470) | 99,606 (172,523) |
| 27 | butyrolactone | 1618 | 1623 | | 2,690,029 (3,731,476) | 329,657 (396,040) | 2,010,119 (2,152,001) | 1,231,611 (505,062) | 1,397,753 (1,178361) | 1,015,098 (500,331) | 703,013 (178,782) |
| 28 | {E}-2-decenal | 1639 | 1641 | | 0 | 0 | 0 | 0 | 249,550 (220,094) | 0 | 0 |

-continued

| | Library/ ID | DB-Wax[b] calc'd | Llt | Source | \multicolumn{7}{c}{Sample Number Relative Abundance[a]} |
|---|---|---|---|---|---|---|---|---|---|---|---|
| PK | | | | | 3 | 6 | 7 | 10 | 11 | 14 | 16 |
| 29 | γ-hexano-lactone | 1692 | 1699 | | 952,362 (438,547) | 970,053 (684 073) | 353,652 (223,661) | 2,274,579 (1,237,162) | 2,100,953 (1,202,468) | 2,826,657 (1,394,652) | 1,137,917 1626,352) |
| 30 | hexanoic acid[d] | 1855 | 1825/1874 | | 1,012,379 (114,604) | 1,270,026 (715,534) | 125,623 (217,586) | 6,939,618 (5,917,223) | 9,909,605 (6,053,143) | 16,080,756 (12,113,509) | 1,598,019 (1,294,180) |
| 31 | γ-octano-lactone | 1907 | 1916 | | 677,789 (239,383) | 523,408 (346,320) | 431,777 (430,702) | 1,458,020 (941,533) | 1,285,430 (638,265) | 2,248,371 (1,146,822) | 935,269 (480,196) |
| 32 | phenol | 2002 | 2000 | | 207,050 (292,713) | 113,533 (101,850) | 89,140 (101,355) | 119,453 (125,360) | 156,471 (140,731) | 198,001 (93,938) | 41,745 (72,304) |
| 33 | γ-nonano-lactone | 2022 | 2030 | | 798,285 (119,068) | 296,827 (180,275) | 341,666 (322,193) | 3,232,200 (3,570,874) | 911,765 (978,572) | 1,017,516 (947,932) | 879,219 (769,904) |
| Aflatoxin Amounts (ppb) | | | | | | | | | | | |
| $B_1$ | Sum | | | | 10.0 (3.7) | 146.0 (232) | 2.9 (1.1) | 26.0 (5.1) | 146.8 (21.5) | 37.8 (14.1) | 66.6 (1.8) |
| $B_2$ | Sum | | | | 2.1 (1.1) | 19.5 (3.0) | 0.3 (0.2) | 3.8 (0.8) | 19.8 (3.3) | 6.4 (0.8) | 9.6 (0.2) |
| $G_1$ | Sum | | | | 3.5 (1.9) | 1.8 (0.3) | 0.3 (0.3) | 1.1 (0.4) | 131.7 (11.1) | 1.5 (2.2) | 18.0 (7.4) |
| $G_2$ | Sum | | | | 0.9 (0.5) | 0.3 (0.2) | 0.1 (0.1) | 0.1 (0.1) | 19.8 (1.1) | 0.0 (0.0) | 3.5 (0.5) |
| Total Aflatoxin Sum | | | | | 16.5 (7.2) | 167.5 (26.2) | 3.6 (1.1) | 30.9 (6.0) | 318.1 (275) | 45.7 (15.1) | 97.6 (3.8) |

[a]Sample numbers as provided and analyzed blindly. Relative amounts are peak surface areas generated by ChemStation ® software. Values in parentheses are standard deviations of triplicates.
[b]Compound identification by RI relative to n-alkanes on DB-Wax column, retention times, mass fragment libraries. and comparison to authentic samples.
[c]Volatiles that displayed relatively large increases in $G_1$ contaminated samples.
[d]Volatiles that were relatively unique in $G_1$ contaminated samples.

Because samples 7 and 14 contained fungi other than aspergilli, data from samples 11 and 16 were further separated and evaluated. The volatile combination of (E)-2-decenal and 1-octen-1-ol once again provided a good correlation with $R^2$ values of 0.56 to AFG1, 0.57 to AFG2, 0.77 to AFB1, and 0.78 to AFB2. Sample 11 contains the largest amount of all aflatoxins in the blanched series and was the only sample to emit (E)-2-decenal.

The data from the non-blanched almond analyses provided better correlations of individual volatiles to aflatoxin content, relative to the blanched or full data set. Interesting was the re-emergence of several compounds initially seen in the early graph of volatile comparisons (FIG. 2) and that showed increases of more than 250% when compared to volatile emissions of samples with no AFG1 and AFG2 (vide supra). The compounds hexanal, 2-butyl furan, heptanal, octanal, and nonanal individually showed $R^2$ values between 0.25 and 0.42 to AFG1 and AFG2. The volatile (E)-2-octenal was unique to sample 13 and showed a correlation to AFG2 with an $R^2$ value 0.71 when evaluated. It was also detected in sample 15B which had a corresponding AFG2 content of 0.1 ppb.

Because the $C_6$-$C_{10}$ aldehydes exhibited continued presence in the data analysis their volatile amounts were combined and evaluated for correlation to AFG2. The non-blanched samples that contained AFG2 (9, 13, and 18) were chosen and compared to the aldehydes and provided the $R^2$ value of 0.62. Interestingly, when these same aldehydes were compared to the AFB2 content in samples 9, 13, and 18 a similar $R^2$ value of 0.61 was obtained; compared to the AFB1 and AFG1 $R^2$ values of 0.47 and 0.43, respectively. The parallel correlation results for AFG2 and AFB2.

A final analysis was performed on the samples in regard to AFG1 and AFG2 content. All of the samples that contained zero AFG2 content were analyzed for correlation of the alkanal volatile amounts to AFG1 (samples 1, 2, 4, 5, 8, 12, 14, and 19-21), and were found to show an $R^2$ value 0.63 suggesting correlation to either aflatoxigenic or non-toxigenic strains.

Returning to the idea of substantial increases in volatile output (greater than 250%) discussed earlier, the volatile amounts for the samples containing zero AFG1 (samples 1A, 1C, 4C, 5A-C, 7B, 8A, 8C, 12B, 12C, 14C, 15C, 17C, 19B, 19C, 20C, 21A, and 21C) were used as a 'zero control' and the corresponding volatiles from all 63 samples (1-21 A-C) were compared for percent increases relative to the zero AFG1 values. When the $C_6$-$C_{10}$ alkanals were monitored for their relative percent increases in each sample 66.7% of the samples were correctly indentified as containing AFG1 and 71.4% of the samples were correctly identified as containing AFG2. The presence of any of the unique volatiles, the $C_8$-$C_{10}$ 2-alkenals, correctly identified a sample as containing AFG1, even though these volatiles were typically in small amounts. One interesting result from this analysis was the correlation of the simultaneous appearance of the three alcohols, 1-hexanol, 1-heptanol, and 1-octanol to AFG1 presence.

Finally, since each sample (1-21) was ground per homogeneity protocols set forth by European commission regulations (see e.g., Commission Regulation (EC) No 401/2006. *Official J. Eur. Union* 2006, L70/12-L7034), it was originally anticipated that the triplicates would be nearly equal in both volatile output and aflatoxin content. However, the large disparity seen between sample replicates provides strong evidence of non-homogeneity.

Using a three-prong approach for the analysis of almonds—volatile emission, aflatoxin content, and CFU counts—correlations were determined to exist between the volatiles hexanal, heptanal, octanal, (E)-2-octenal, 3-octen-2-one, nonanal, (E)-2-nonenal, decanal, and (E)-2-decenal to that of the aflatoxin content in blanched and non-blanched almonds. Thus, the results presented herein provide a unique volatile emission pattern for that of aspergilli contaminated almonds; a volatile pattern that is dissimilar to the current data regarding emissions of in situ, ex situ, and ambient almond volatile analyses.

Example 2

The following Example illustrates an exemplary method for estimating the amount of aflatoxin associated with a given an indicator volatile or volatiles.

Typical Calibration Curve Experiment to Determine Relative Amount of a Volatile.

Determination of Calibration Line for a Compound.

The compound A was attained from a commercial source. Compound A was diluted in hexanes to 0.0125, 0.0250, 0.0500, and 0.1000 molar solutions and transferred to autosampler vials. Injections of 1.0 µL of the compound A solutions were analyzed using an Agilent Technologies 6890N GC coupled to a 5975B inert MS (Santa Clara, Calif.) with a DB-Wax GC column (60 m, 0.320 mm ID, 0.25 µm film; Agilent J&W Scientific, Santa Clara, Calif.). GC-MS Method: injector temp, 200° C.; split (2:1) injection setting, inlet pressure, 11.71 psi; total flow, 6.2 mL/min; split-flow, 2.4 mL/min; helium flow, 1.2 mL/min; average velocity, 29 cm/sec; constant flow; initial temp, 150° C.; hold time, 0 min; ramp 1, 2° C./min; final temp, 160° C.; hold time, 0 min; ramp 2, 20° C./min; final temp, 200° C.; hold time, 3 min; post time 210° C., 2 min. (see e.g., Light, D. M.; Beck, J. J. *J. Agric. Food Chem.* 2010, 58, 7838-7845). Injections were performed in triplicate for each concentration and the averages used to graph relative peak area versus concentration of PE in nanograms. Regression analysis using a linear trendline provided an equation y=mx+b ($R^2$=0.9999, for example) with a determined S/N=20, for example, for the lowest concentration. A limit-of-detection can be estimated (e.g., 0.100 ng.) The limit-of-detection can confirmed by injection (integration corresponding to an amount in ng) of a diluted standard sample at the estimated limit-of-detection concentration and using m/z of fragments corresponding to those of compound A. The regression equations, emission decay curve models, and statistical analyses for all emission experiments can all be computed using standard regression software (e.g., Excel, Microsoft Inc.). The kinetic orders of emissions can be determined by the linearity plots of the logarithmic transformations of emission rates.

Once the relative response of compound A is known via the method of GC-MS, for example, a correlation of the approximate amount of volatile compound A to the amount of aflatoxin (e.g., AFG1, in ppb) within a sample can be inferred. For example, using the equation y=mx+b obtained from the calibration curve for compound A (similar calibration curves must be run for each volatile being detected and used as an indicator volatile), the relative abundance (the y value in the equation) in each sample can be inserted into the equation for compound A. Solving for x then supplies the relative amount of compound A (in pg or ng for example) emitted from the volatile sample.

Correlation of compound A to the amount (e.g., ppb) of aflatoxin (e.g., AFG1): A typical procedure for correlating volatile emission of one or more compounds to that of the aflatoxin content within a sample would be as follows. Using similar procedures described for calibration curves, a particular volatile (e.g., 2-(E)-octental) or set of volatiles (e.g., the alkanals: hexanal, heptanal, octanal, nonanal, and decanal) would be monitored and measured over a range of concentrations of an *Aspergillus* (e.g., *A. parasiticus*) inoculated onto almonds and allowed to culture for an finite time (e.g., 24 h at room temperature). The volatile output would be measured and recorded for several replicates of each concentration, after which time each sample for all replicates at all concentrations would be subjected to aflatoxin content (e.g., in ppb) via known methods in the art. The amount of aflatoxin (e.g., AFG1) would then be graphed against the volatile output for the individual and/or sum of volatiles examined (e.g., 2-(E)-octenal or the alkanals previously noted). If true indirect correlation exists between the volatile and aflatoxin (e.g., AFG1) linear regression analysis of the graphed material will provide a high correlation (e.g., high $R^2$ value) and the corresponding equation can then be utilized in similar fashion as described previously to draw an indirect correlation between the amount of volatile emitted and the amount of aflatoxin present in the sample.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for detecting the presence of at least one aflatoxin in a crop or crop product, wherein the aflatoxin is produced by an aflatoxigenic *Aspergillus* species, and wherein the aflatoxigenic *Aspergillus* species is co-existent with other fungal species in a natural fungal bouquet, the method comprising:

(i) determining a volatile emission profile of the crop or crop product, and (ii) comparing the volatile emission profile of the crop or crop product to a volatile emission profile of a control crop or crop product that is known or designated as aflatoxin free, and (iii) detecting the presence of at least one unique volatile indicator species in the volatile emission profile of the crop or crop product that is not present in the volatile emission profile of the control crop, wherein the presence of the at least one unique volatile indicator species in the volatile emission profile of the crop or crop product that is not present in the volatile emission profile of the control crop or crop product, indicates that the crop or crop product is contaminated with aflatoxins, wherein the at least one unique volatile indicator species is a member selected from the group consisting of (E)-2-octenal, (E)-2-nonenal, and (E)-2-decenal.

2. The method of claim 1, wherein the volatile emission profile of the crop or crop product and the volatile emission profile of the control crop or crop product comprise hexanal, heptanal, octanal, 3-octen-2-one, nonanal, and decanal, and wherein the comparing of the volatile emission profile of the crop or crop product to the volatile emission profile of the control crop or crop product reveals that the amount of hexanal, heptanal, octanal, 3-octen-2-one, nonanal, and decanal is increased in the crop or crop product by comparison to the control crop or crop product, thereby indicating that the crop or crop product is contaminated with aflatoxins.

3. The method of claim 2, wherein the amount of hexanal, heptanal, octanal, 3-octen-2-one, nonanal, and decanal is increased in the crop or crop product by at least about 200% by comparison to the control crop or crop product.

4. The method of claim 1, wherein the crop or crop product is a tree nut crop, and the control crop or crop product that is known or designated to be aflatoxin free is a tree nut crop.

5. The method of claim 4, wherein the tree nut crop is an almond crop, and the control tree nut crop that is known or designated to be aflatoxin free is an almond crop.

6. The method of claim 1, wherein the volatile emission profile is generated using a Gas Chromatograpy/Mass Spectrometry (GC-MS) instrument.

7. The method of claim 6, wherein the GC-MS instrument is portable.

8. The method of claim 1, wherein the method is practiced on post harvest tree nuts.

9. The method of claim 8, wherein the post harvest tree nuts are post harvest almonds.

10. The method of claim 9, wherein the post harvest tree nuts are in wind-swept rows.

11. The method of claim 9, wherein the post harvest tree nuts are contained within a storage and/or shipping container.

12. The method of claim 1, wherein the crop or crop product is cotton and the control crop or crop product is cotton.

13. A method for detecting the presence of at least one aflatoxin in an almond crop,
wherein
the aflatoxin is produced by an aflatoxigenic *Aspergillus* species, and wherein
the aflatoxigenic *Aspergillus* species is co-existent with other fungal species in a natural fungal bouquet,
the method comprising:
(i) determining a volatile emission profile of the almond crop, and
(ii) comparing the volatile emission profile of the almond crop to a volatile emission profile of a control almond crop that is known or designated as aflatoxin free, and
(iii) detecting the presence of at least one unique volatile indicator species in the volatile emission profile of the almond crop that is not present in the volatile emission profile of the control almond crop,
wherein
the presence of the at least one unique volatile indicator species in the volatile emission profile of the almond crop that is not present in the volatile emission profile of the control almond crop, indicates that the almond crop is contaminated with aflatoxins,
wherein
the at least one unique volatile indicator species is a member selected from the group consisting of (E)-2-octenal, (E)-2-nonenal, and (E)-2-decenal.

14. The method of claim 13, wherein the volatile emission profile of the almond crop and the volatile emission profile of the control almond crop comprise hexanal, heptanal, octanal, 3-octen-2-one, nonanal, and decanal, and
wherein
the comparing of the volatile emission profile of the almond crop to the volatile emission profile of the control almond crop reveals that the amount of hexanal, heptanal, octanal, 3-octen-2-one, nonanal, and decanal is increased in the almond crop by comparison to the control almond crop,
thereby
indicating that the almond crop is contaminated with aflatoxins.

15. The method of claim 14, wherein the amount of hexanal, heptanal, octanal, 3-octen-2-one, nonanal, and decanal is increased in the almond crop by at least about 200% by comparison to the control almond crop.

16. The method of claim 13, wherein the volatile emission profile is generated using a Gas Chromatograpy/Mass Spectrometry (GC-MS) instrument.

17. The method of claim 16, wherein the GC-MS instrument is portable.

* * * * *